(12) United States Patent
Belew et al.

(10) Patent No.: US 7,423,124 B2
(45) Date of Patent: Sep. 9, 2008

(54) METHOD FOR ALBUMIN PURIFICATION

(75) Inventors: Makonnen Belew, Uppsala (SE); Mei Yan Li, Shijiazhuang (CN); Wei Zhang, Shijiazhuang (CN)

(73) Assignee: Ge Healthcare Bio-Sciences AB, Uppsala (SE)

(*) Notice: Subject to any disclaimer, the term of this patent is extended or adjusted under 35 U.S.C. 154(b) by 262 days.

(21) Appl. No.: 10/514,536

(22) PCT Filed: May 9, 2003

(86) PCT No.: PCT/SE03/00766

§ 371 (c)(1),
(2), (4) Date: May 25, 2005

(87) PCT Pub. No.: WO03/097692

PCT Pub. Date: Nov. 27, 2003

(65) Prior Publication Data

US 2005/0214902 A1    Sep. 29, 2005

(30) Foreign Application Priority Data

May 15, 2002   (SE)   .................................... 0201518

(51) Int. Cl.
*C07K 1/00* (2006.01)
(52) U.S. Cl. ..................................................... 530/364

(58) Field of Classification Search ........................ None
See application file for complete search history.

(56) References Cited

U.S. PATENT DOCUMENTS 5,440,018 A * 8/1995 Ohmura et al. ............. 530/363

FOREIGN PATENT DOCUMENTS

| EP | 0 570 916 | 5/1993 |
| EP | 0 612 761 | 2/1994 |
| WO | WO 02/05959 | 1/2002 |

* cited by examiner

*Primary Examiner*—Robert B. Mondesi
(74) *Attorney, Agent, or Firm*—Yonggang Ji

(57) ABSTRACT

The present invention is a method of purifying recombinant human serum albumin (rHSA) from a solution, which method comprises to subject a cell culture supernatant (CCS) comprising rHSA cation exchange on a bimodal high salt tolerant matrix; hydrophobic interaction chromatography (HIC); anion exchange; and recovering the purified rHSA. The bimodal high salt tolerant cation exchange matrix used enables performing a purification of a cell culture supernatant directly, in the sense that no further dilution thereof is necessary. Due to its high binding capacity, said bimodal cation exchange matrix also allows use of a smaller amount of matrix as compared to a corresponding conventional cation exchanger matrix. Accordingly, the present invention allows substantial savings as regards volumes and consequently operation costs.

12 Claims, 4 Drawing Sheets n = 0-10

METHOD FOR ALBUMIN PURIFICATION

CROSS REFERENCE TO RELATED APPLICATIONS

This application is a filing under 35 U.S.C. §371 and claims priority to international patent application number PCT/SE03/00766 filed May 9, 2003, published on Nov. 27, 2003 as WO 03/097692 and also claims priority to patent application number 0201518-8 filed in Sweden on May 15, 2002.

TECHNICAL FIELD

The present invention relates to the field of protein purification, and especially to the purification of human serum albumin. The method utilises a series of chromatography steps, which results in an efficient purification suitable for use in large-scale operations.

BACKGROUND

Human serum albumin (HSA) is the most abundant protein present in blood plasma, where its role is to contribute to the maintenance of osmotic pressure and to bind nutrients and metabolites, to thereby enable transport thereof. There is a large pharmaceutical and scientific interest in HSA, e.g. as a drug for treating hypoalbuminemia caused by a loss of albumin or a reduction in albumin synthesis, in hemorrhagic shock etc. In the earliest methods available, the HSA was purified from blood. However, such methods brought about problems, for example a sporadic supply of blood, economical disadvantages and contamination with undesirable substances such as hepatitis virus and not least AIDS virus. To avoid these problems, alternative methods based on recombinant DNA techniques have more recently been developed to produce recombinant HSA (rHSA). Even though a number of recombinant methods have been suggested, it has been shown that the purification of the rHSA from the fermentation broth is a crucial step and there is an ongoing need of improvements to this end.

EP 0 612 761 discloses a method of producing recombinant human serum albumin of high purity, which does not contain free non-antigenic contaminants. The method utilises hydrophobic interaction chromatography (HIC) under specified conditions combined with other steps such as ion exchange chromatography, treatment with boric acid or a salt thereof followed by ultrafiltration, and heat treatment. However, a series of that many steps will still be too complex and accordingly too expensive for satisfactory use in large-scale operation in industry.

EP 0 570 916 also discloses a process for producing recombinant human serum albumin by gene manipulation techniques, wherein purification is by a combination of steps in which a culture supernatant is subjected to ultrafiltration, heat treatment, acid treatment and another ultrafiltration, followed by subsequent treatments with a cation exchanger, a hydrophobic chromatography carrier and an anion exchanger and by salting out. However, similar to the above-mentioned patent, this purification scheme is too complex, time-consuming and accordingly too expensive to provide an efficient procedure for use in large-scale operation.

EP 0 699 687 discloses a method of purification of rHSA wherein culture medium is heat treated to inactivate proteases and then contacted with a fluidised bed of cation exchange particles. The eluent can subsequently be subject to ultrafiltration, HIC and anion exchange chromatography. However, use of a fluidised bed will require equipment different to the conventional packed bed chromatographic step. Accordingly, there is still a need of more efficient and economically attractive procedures for purification of rHSA from a culture broth.

SUMMARY OF THE INVENTION

One object of the present invention is to provide a method for purification of recombinant HSA that is easily adapted to large-scale operation. This is achieved by a method, which comprises subjecting a cell culture supernatant (CCS) comprising rHSA to the following steps:
(a) cation exchange chromatography on a bimodal high salt tolerant matrix;
(b) hydrophobic interaction chromatography (HIC);
(c) anion exchange chromatography.

The method according to the invention comprises fewer process steps than the above-discussed methods. In addition, the bimodal high salt tolerant cation exchange matrix used in step (a) allows use of a cell culture supernatant without any further dilution, which is an advantageous feature since it greatly reduces the total volume and hence the costs as compared to the prior art methods.

Another object of the invention is to improve the adsorption capacity of the chromatographic steps used in purification of rHSA. This can be achieved by the method described above wherein a cation exchanger, comprising ligands known as high salt ligands (HSL), is used in step (a). Said ligands are bimodal in the sense that they comprise at least two sites that interact with the substance to be isolated, one providing a charged interaction and one providing an interaction based on hydrogen bonds and/or a hydrophobic interaction.

Another object of the invention is to further decrease the colour content, and more specifically to further increase the purity, of the final product. This can be achieved by use of the method described above, wherein a weak anion exchanger is used.

DETAILED DESCRIPTION OF THE INVENTION

Figure 1A:
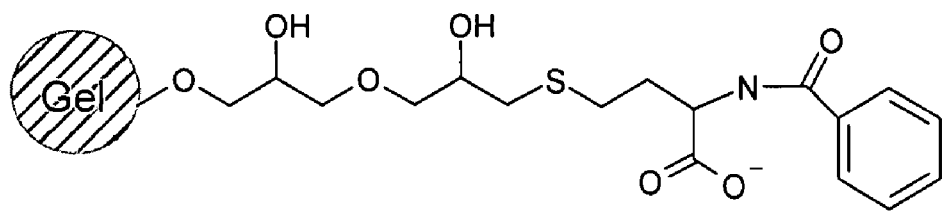
FIG. 1A-D illustrates possible matrix materials suitable for use in the different steps of cation exchange, hydrophobic interaction and anion exchange chromatography according to the invention.

One aspect of the present invention is a method of purifying recombinant human serum albumin (rHSA) from a solution, which method comprises subjecting a cell culture supernatant (CCS) comprising rHSA to the following chromatographic steps
(a) cation exchange on a bimodal high salt tolerant matrix;
(b) hydrophobic interaction chromatography (HIC); and
(c) anion exchange.

In a specific embodiment of the present method, the conductivity of the CCS is above about 10 mS/cm, such as above about 15 and preferably above about 20, e.g. about 25-50, or more specifically 25-30 mS/cm, when applied to step (a), which is possible due to the kind of cation exchanger used, which comprises ligands of the type known as high salt ligands (HSL). Accordingly, an important advantage with the present method is that it avoids the need to dilute the CCS, and thereby allows use of much reduced volumes of sample during the cation exchange step as compared to the previously described methods for purification of rHSA.

The CCS can be any fermentation broth from which cells preferably have been removed e.g. by centrifugation. Accordingly, the origin of the rHSA isolated according to the present invention can be any suitable host, such as microbial cells, such as *Escherishia coli, Bacillus subtilis* etc, yeast cells, such as *Saccharomyces cerevisiae, Pichia pastoris* etc, or animal cell lines. In an advantageous embodiment, the host cell is *Pichia pastoris*. Methods of producing a recombinant host cell and conditions for expression of a protein such as rHSA therefrom are well known, see e.g. the above discussed EP 0 612 761 for a reference to various patent applications within this field.

The main purpose of step (a) is to eliminate low molecular weight coloured substances such as pigments that are negatively charged. Thus, step (a) utilises a cation exchanger, which comprises ligands of the type known as high salt ligands (HSL). In this context, "high salt" refers to the above-mentioned property of high salt concentration tolerance that is characteristic for this class of ion exchangers. This property is provided by the nature of the ligands, which is bimodal in the sense that each ligand comprises two groups capable of interacting with the substance to be isolated, in the present case rHSA. The primary binding mode is provided by a charged binding group, i.e. an ion exchanging group, hence the classification of the HSL-type of matrices as ion exchangers. A second binding mode is provided by a secondary binding group, which provides an additional interaction with the substance to be isolated. Usually, the secondary binding group provides a hydrogen bonding or a hydrophobic interaction, but other interactions can be envisaged, as will be discussed in more detail below. In this context, it is to be noted that the term "bimodal" is used herein to define that two or more binding modes are involved, and it is therefore not limited to only two binding modes. In the present application, cation exchangers of HSL-type are utilised, and such cation exchangers have been disclosed in detail, see e.g. PCT/EP01/08203 (Amersham Pharmacia Biotech AB). However, a general description thereof will follow below.

The charged binding group present on a cationic high salt ligand (HSL) can be selected from the group comprised of sulphonate ($-SO_3^-/-SO_3H$), sulphate ($-OSO_3^-/-OSO_3H$), carboxylate ($-COO^-/-COOH$), phosphate ($-OPO_3^{2-}/-OPO_3H^-/-OPO_3H_2$ and phosphonate ($-PO_3^{2-}/-PO_3^-H/-PO_3H_2$). In one advantageous embodiment, the HSL-type of cation exchanger is a weak cation-exchanger, i.e. cation-exchangers that have a pKa above 3. In an alternative embodiment, they are strong cation exchangers that have a pKa below 3. Typical examples of such weak cation exchangers are carboxylate ($-COO^-/-COOH$), phosphate ($-OPO_3^{2-}/-OPO_3H^-/-OPO_3H_2$ and phosphonate ($-PO_3^{2-}/-PO_3H^-/-PO_3H_2$).

The secondary binding group comprises at least one hydrogen-bonding atom, which is located at a distance of 1-7 atoms from the cation-exchanging group. A hydrogen-bonding atom is an atom that is capable of participating in hydrogen bonding (except hydrogen), see Karger et al., An Introduction into Separation Science, John Wiley & Sons (1973) page 42. The hydrogen-bonding atom can be selected from the group that consists of heteroatoms, such as oxygens (carbonyl oxygen, ether oxygen, ester oxygen, hydroxy oxygen, sulphone oxygen, sulphone amide oxygen, sulfoxide oxygen, oxygen in aromatic rings etc), nitrogens (amide nitrogen, nitrogen in aromatic rings etc), sulphurs (thioether sulphur, sulphur in aromatic rings etc); and sp- and sp$^2$-hybridised carbons; and halo groups, such as fluoro, chloro, bromo or iodo, preferably fluoro. The second binding group typically contains no charged atom or atom that is chargeable by a pH change.

The stability of the cation exchange ligands used in step (a) can in general terms be defined as the capacity to resist 0.1 or 1 M NaOH in water for at least 40 hours. For illustrative examples of suitable chemical ligand structures of the cation exchangers useful in step (a) of the present method, see above-mentioned PCT/EP01/08203. In a specific embodiment of the present method, step (a) utilises the HSL cation exchange ligand illustrated in FIG. 1A of the present specification.

Defined in functional terms, the cation-exchanger used in step (a) of the present method is capable of
(a) binding rHSA by cation-exchange in an aqueous reference liquid at an ionic strength corresponding to 0.3 M NaCl and,
(b) permitting a break through capacity for the substance ≧200%, such as ≧300% or ≧500% or ≧1000%, of the break through capacity of the substance for a reference cation-exchanger containing sulphopropyl groups $-CH_2CH_2CH_2SO_3^-$ at the ionic strengths shown above.

PCT/EP01/08203 describes such a reference ion exchanger in more detail. The level of cation-exchange ligands in the cation-exchangers used in the inventive method is usually selected in the interval of 1-4000 µmol/ml matrix, such as 2-500 µmol/ml matrix, with preference for 5-300 µmol/ml matrix. Possible and preferred ranges are, among others, determined by the nature of the matrix, ligand etc. Thus, the level of cation-exchange ligands is usually within the range of 10-300 for agarose-based matrices. For dextran-based matrices, the interval is typically 10-600 µmol/ml matrix.

The above mentioned PCT/EP01/08203 also comprises an extensive discussion of matrix materials useful with cation exchangers of HSL-type. In brief, such matrices can be based on organic or inorganic material. It is preferably hydrophilic and in the form of a polymer, which is insoluble and more or less swellable in water. Hydrophobic polymers that have been derivatized to become hydrophilic are included in this definition. Suitable polymers are polyhydroxy polymers, e.g. based on polysaccharides, such as agarose, dextran, cellulose, starch, pullulan, etc. and completely synthetic polymers, such as polyacrylic amide, polymethacrylic amide, poly (hydroxyalkylvinyl ethers), poly(hydroxyalkylacrylates) and polymethacrylates (e.g. polyglycidylmethacrylate), polyvinylalcohols and polymers based on styrenes and divinylbenzenes, and co-polymers in which two or more of the monomers corresponding to the above-mentioned polymers are included. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on co-polymers of monovinyl and divinylbenzenes) by polymerisation of monomers exhibiting groups which can be converted to OH, or by hydrophilisation of the final polymer, e.g. by adsorption of suitable compounds, such as hydrophilic polymers. An illustrative example of a suitable matrix is the commercially available beaded Sepharose, which is agarose-based and available from Amersham Biosciences, Uppsala, Sweden. Suitable inorganic materials to be used as support matrices are silica, zirconium oxide, graphite, tantalum oxide etc.

The above mentioned PCT/EP01/08203 comprises an extensive disclosure of the preparation of cation exchangers of HSL-type. Also, a review of methods of immobilising ligand-forming compounds to surfaces is given in Hermanson, G. T., Mallia, A. K. & Smith, P. K., (Eds.), *Immobilisation Affinity Ligand Techniques*, Academic Press, INC, 1992.

As mentioned above, one of the benefits of the HSL-type of ion exchangers is that it is possible to run adsorption to the column, i.e. binding of rHSA to the ligand, at elevated ionic strengths compared to what has normally been done for conventional cation-exchangers, for instance the reference sulphopropyl cation-exchanger discussed above. The exact ionic strength to be used during binding depends on the nature of the protein and the type and concentration of the ligand on the matrix. Useful ionic strengths often correspond to NaCl concentrations (pure water)$\geq 0.1$ M, such as $\geq 0.3$ M or even $\geq 0.5$ M. Desorption can be performed e.g. by increasing the ionic strength and/or by change of the pH. Typical salts to be used for changing the ionic strength are selected among soluble ammonium or metal salts of phosphates, sulphates, etc, in particular alkali metal and/or alkaline earth metal salts. The same salts can also be used in the adsorption steps, but then often in lower concentrations.

In one embodiment of the present method, the amount of cation exchange matrix used in step (a) is about half the amount of HIC matrix used in step (b). Accordingly, one advantage of the present invention is the outstanding binding capacity of the bimodal cation exchange matrix that allows a reduction in volume and therefore operational costs as compared to conventional cation exchangers. In the presence of a high salt concentration, such as a conductivity of about 25-30 mS/cm, the adsorption of commercially available SP Sepharose for rHSA is about 2-4 mg/mL packed gel, while that of the high salt ligand prototype (FIG. 1A) has been shown to be at least 50 mg/mL. Accordingly, the use of the bimodal high salt ligand (HSL) clearly simplifies and improves the purification process significantly and reduces the cost of operation on large scale.

One embodiment of the present method comprises heat treatment of the CCS before step (a). The heating can be performed directly i.e. while the host cells are still present or after removal thereof, such as by centrifugation, ultrafiltration or any other suitable method. The heating can be performed at 50-100° C. during a period of time of from 1 minute up to several hours, preferably at 60-75° C. for 20 minutes to 3 hours and most preferably at about 68° C. for about 30 minutes. The heating is conveniently performed in a water bath equipped with thermostat. In one embodiment, a stabiliser is added before the heating, such as sodium caprylate at a pH of about 6.0. Other stabilisers can be used, such as acetyltryptophan, organic carboxylic acids etc. After the heating, the pH of the CCS is preferably adjusted to a lower value suitable for the subsequent adsorption on a cation exchanger, such as pH 4.5.

In another embodiment of the present method the product from step (a), i.e. the fraction bound to the column comprising the HSL-type matrix, is heat-treated before step (b). Preferably, a reducing agent, such as cysteine, is added. Other examples of useful reducing agents are mercaptoethanol, reduced glutathione etc. The purpose of this is to facilitate the removal of coloured substances during step (b). This heat treatment is in general performed as described above, even though in the preferred embodiment, a slightly lower temperature such as about 60° C. for a slightly longer period of time such as about 60 minutes is used.

As mentioned above, step (b) of the present method utilises hydrophobic interaction chromatography (HIC). The main purpose of step (b) is to remove proteolytic degradation products of rHSA, which products are usually of a size of about 10-50 kDa. HIC is a well-known principle in the art of chromatography, and provides a versatile tool for separation based on differences in surface hydrophobicity. Many biomolecules that are considered to be hydrophilic have been shown to still expose sufficient hydrophobic groups to allow interaction with the hydrophobic ligands attached to the chromatographic matrix. HIC has already been suggested for the purification of rHSA, see e.g. EP 0 699 687. Compared with another well known separation principle, namely reverse phase chromatography, HIC utilises a much lower density of ligand on the matrix. This feature promotes a higher degree of selectivity, while allowing mild elution conditions to help preserve the biological activity of the protein of interest. In the present context, the HIC step is used to adsorb the above-mentioned proteolytic degradation products of rHSA, while the full length rHSA is eluted in the unbound fraction. The hydrophobic interaction between the rHSA and the immobilised ligand on the matrix is enhanced by a small increase in the ionic strength of the buffers used. There are many separation materials commercially available for HIC today, and the present invention is not limited to any specific matrix and/or ligand. Thus, in general terms, the matrix used in step (b) can be based on an organic or inorganic material. In the case of organic materials, it can e.g. be a native polymer, such as agarose, dextran, cellulose, starch etc, or a synthetic polymer, such as divinylbenzene, styrene etc. In the case of inorganic matrix materials, silica is a well-known and commonly used material. In an advantageous embodiment, the matrix is cross-linked agarose, which is commercially available from a number of companies, such as Sepharose™ from Amersham Biosciences (Uppsala, Sweden). In one embodiment, the HIC matrix used in step (b) exhibits one or more hydrophobic ligands capable of interaction with rHSA, selected from the group that consists of phenyl, butyl, such as n-butyl, octyl, such as n-octyl, etc, preferably on an agarose matrix. Alternatively, hydrophobic ligands such as ethers, isopropyl or phenyl are present on a divinylbenzene matrix, such as Source™ from Amersham Biosciences (Uppsala, Sweden). In the most preferred embodiment, phenyl ligands on a crosslinked agarose matrix are used for step (b). The matrix is preferably comprised of porous beads, which can have a water content of above about 90%, preferably about 94%. The average particle size can e.g. be between 10 and 150 μm as measured on a wet bead, preferably below 100, such as about 90 μm. The ligand density on the matrix can for example be between 20 and 60, such as about 40 μmol/ml gel. As a specific example, the matrix used is Phenyl Sepharose™ 6 Fast Flow from Amersham Biosciences (Uppsala, Sweden). In this specific case, the denotation Fast Flow is used for a matrix the cross-linking of which has been optimised to give process adapted flow characteristics with typical flow rates of 300-400 cm/h through a 15 cm bed height at a pressure of 1 bar. However, the skilled person in this field can easily adapt such process parameters depending on the scale of the operation. This step can be performed at a pH of about 4-8, such as 6.5-7, and at a salt concentration of about 0.01 to 0.5 M, such as 0.05 to 0.2 M.

As is also mentioned above, step (c) of the present method utilises an anion exchanger, preferably a weak anion exchanger, for removing minor impurities from step (b), and especially to remove undesired compounds, such as low molecular weight pigments. The invention is not limited to use of any specific anion exchanger material, as long as it exhibits a sufficient amount of ligands capable of binding compounds of negative charge that are undesirable in the final rHSA product. The anion exchange chromatographic step can e.g. be performed at a pH of about 5.0-8.0 and a salt concentration of 0.01 to 0.2 M for removal of the impurities. As regards the matrix material, it may be of any organic or inorganic material, as discussed above. In one preferred embodiment, the matrix is comprised of porous beads of cross-linked agarose, such as Sepharose™ from Amersham Biosciences (Uppsala, Sweden). The ligands attached thereto are weak anion exchangers, the binding group of which is for example a primary or secondary amine. Such a binding group can be attached to the matrix e.g. via an alkyl chain with an ether group closest to the matrix. The literature describes many ways of attaching a binding group to a matrix via spacers, arms etc, and as mentioned above the present invention is not limited to any specific structure. In an illustrative embodiment, an agarose bead having ligands according to the following formula —O—$CH_2CH_2$—$N^+(C_2H_5)_2H$, e.g. DEAE Sepharose™ from Amersham Biosciences, is used. This embodiment will result in rHSA in both the bound and the unbound fraction eluted from the column which, for some applications, is satisfactory.

However, an alternative embodiment which is more advantageous as far as purity of the final product is concerned, is using an agarose bead having ligands that comprise two ester groups, and preferably also two hydroxyl groups. The binding group is then preferably primary amine. The advantage with this embodiment is that the rHSA will be present only in the fraction that is moderately bound to the matrix, resulting in a much-improved purity and operational convenience. An illustrative general formula for this last mentioned embodiment is presented in FIG. 1, however it is to be understood that the present invention also comprises a method wherein similar structures are used in step (c).

However, it is to be understood that the present invention encompasses use also of matrices similar to the above, which are based on the same general ligand structure. Also, the denotation "Gel" in the formula of FIG. 1A is understood to include any matrix, as discussed above in relation to step (b). One commercially available example of a matrix comprising the above-described ligand is ButylSepharose™ (Amersham Biosciences, Uppsala, Sweden). In the experiments presented below, a ligand density of 160 µmoles/ml was used. Accordingly, it appears that especially advantageous results can be achieved by optimising the ligand density of the matrix. It also appears that when the first mentioned kind of anion exchangers are used, i.e. DEAE-kind of matrices, a larger volume is required, such as about three times the volume, as compared to the last mentioned Butyl-Sepharose media. Accordingly, the preferred embodiment of the present method utilises a secondary amine as the anion-exchanging group during step (c) and a ligand density of at least about 100 µmoles/ml.

In a specific embodiment, the ligand density of the anion exchanger is in the range of 50-300, such as 100-200 and preferably about 160 µmoles/ml. One advantage is that the purified rHSA can then be recovered only from the bound fraction from step (c), as compared to e.g. DEAE when it may be present in both bound and unbound fractions.

DETAILED DESCRIPTION OF DRAWINGS

Figure 1B:
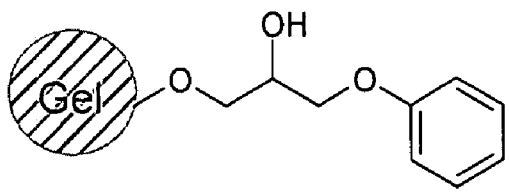
Figure 1C:
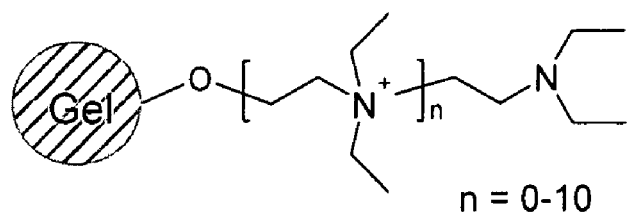
Figure 1D:
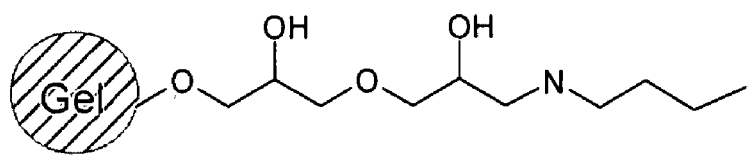

FIG. 1A-D illustrates possible ligand structures suitable for use in the present method. More specifically, FIG. 1A shows a cation exchanger of high salt ligand (HSL) type, FIG. 1B shows a hydrophobic interaction chromatography matrix namely Phenyl Sepharose, and FIGS. 1C and 1D show two alternative anion exchangers namely a generalised formula including the structure of the commercially available DEAE Sepharose (FIG. 1C when n=0) and the modified butyl-Sepharose, which comprises an increased ligand density, as described below.

Figure 2:
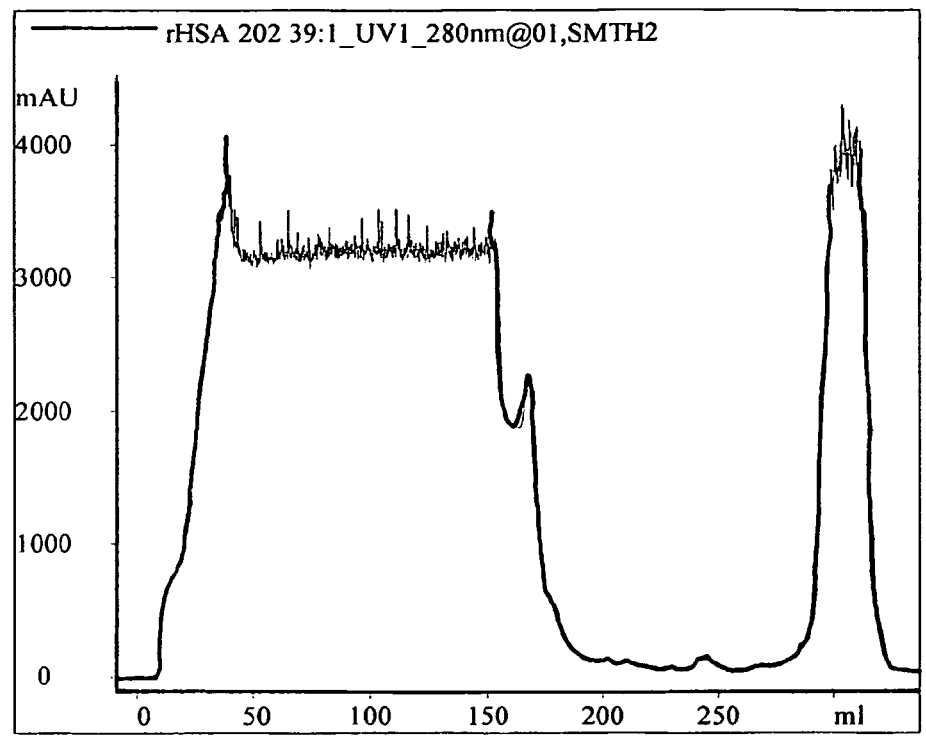
FIG. 2 shows the results of cation exchange chromatography according to step (a) of the method according to the invention of an undiluted cell culture supernatant (CCS). Fraction 2B contains the rHSA.

FIG. 2 shows the results from step (a), i.e. cation exchange chromatography of 147 mL undiluted cell culture supernatant (CCS) on a 20 mL column comprising a cation exchange matrix with the ligand structure illustrated in FIG. 1A. Fraction 1B contains the rHSA, which is clearly separated from the impurities represented by fraction 2A.

Figure 3:
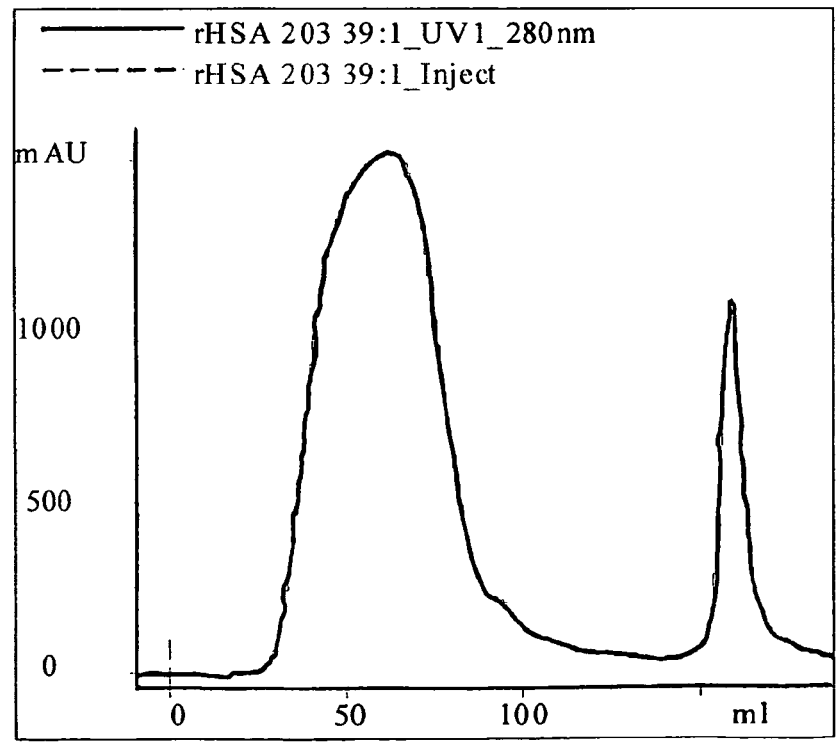
FIG. 3 shows the results of HIC of fraction 2B from FIG. 2. The rHSA is eluted in fraction 3A.

FIG. 3 shows the results from step (b), i.e. hydrophobic interaction chromatography (HIC) of fraction 2B from FIG. 2 on a 40 ml column comprising Phenyl Sepharose as illustrated in FIG. 1B. Fraction A represents the rHSA.

Figure 4:
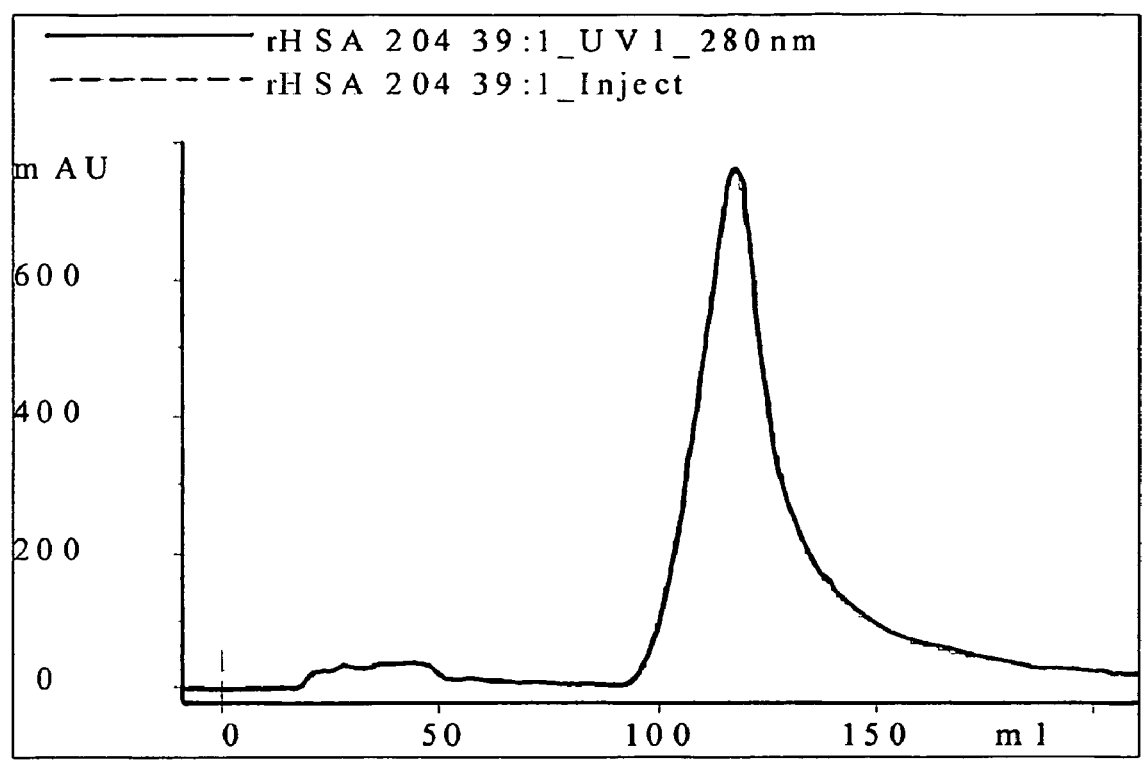
FIG. 4 shows the results of anion exchange chromatography of fraction 3A from FIG. 3. The purified rHSA is eluted in fraction 4B.

FIG. 4 shows the results from step (c), i.e. anion chromatography of fraction 3A from FIG. 3 on a 40 ml column comprising the modified butyl-Sepharose as described in the experimental part below. The purified rHSA is in fraction 4B.

Figures 5A, 5B, 5C:
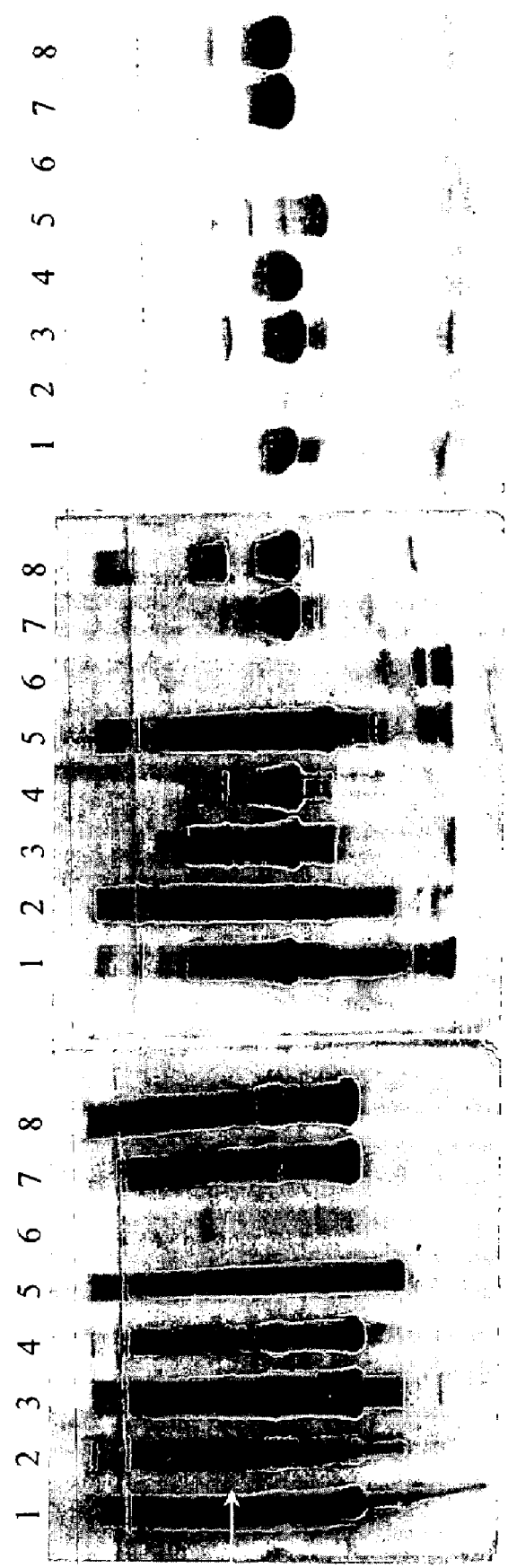
FIG. 5 shows electrophoresis analyses of the main fractions obtained using the three step purification protocol according to the present invention.

FIG. 5 shows native PAGE (8-25%) and SDS-PAGE (10-15%) analyses of the main fractions obtained using the three step method according to the invention. For native PAGE visualised by silver staining (5A), about 3.3 µg of protein per spot was applied. For SDS-PAGE visualised by silver staining (5B), about 2 µg of protein per spot was applied. For SDS-PAGE visualised by Coomassie staining (5C), about 10 µg of protein per spot was applied. 1: CCS; 2: HSL Cat. Ex. (unbound); 3: HSL Cat. Ex. (bound); 4: Phenyl (unbound); 5. Phenyl (bound); 6: HiSub. Butyl; 7: HiSub. Butyl (bound); 8: HSA (control). The arrows show the positions of rHSA.

EXPERIMENTAL PART

Materials and Methods

The cell culture supernatant (CCS) containing rHSA was prepared by fermenting genetically-modified *P. pastoris* cells for 2 weeks or more, followed by separation of the cells by filtration. The CCS, which was green in colour, was divided into aliquots of about 200 ml and stored at −20° C. until use. The quality of the CCS was determined by gel filtration on an analytical column of Superdex™ 200 HR 10/30 (Amersham Biosciences, Uppsala, Sweden). This analysis gave the relative amounts of high molecular weight (HMW) and low molecular weight (LMW) impurities in the CCS as well as the approximate content of the monomeric form of rHSA.

Sodium caprylate (octanoic acid, Na salt) and L-cysteine were bought from SIGMA Chemical Co. Chromatographically purified HSA from human plasma was kindly provided by I. Andersson at the plasma processing unit of Amersham Biosciences, Uppsala, Sweden. The concentration of protein in various samples was determined using the BioRad Protein Assay kit (known as the Bradford method). Bovine serum albumin (BSA) was used to construct the standard curve. UV/is absorption measurements were made using a Shimadzu UV-160A recording spectrophotometer (Shimadzu Corporation, Japan). All other chemicals used were of analytical or reagent grade.

Analytical electrophoresis was performed using a Phastgel electrophoresis system and appropriate PhastGel media and buffer Strips (all from Amersham Biosciences, Uppsala, Sweden). The electrophoretic analyses were performed using native-PAGE (8-25%) or SDS-PAGE (non-reduced, 10-15%) gels according to the Manufacturer's recommendations. The amount of sample applied per spot was as follows: about 3.3 µg for native samples and 2 µg for the SDS-treated samples, both of which were stained with Silver Staining Kit (Amersham Biosciences, Uppsala, Sweden); 10 µg for the SDS-treated samples that were stained with Coomassie Brilliant Blue (CBB).

Mass spectrometric analysis (aimed at determining the mass of purified rHSA and plasma-derived HSA) were done by Dr. J. Flensburg at Amersham Biosciences, Uppsala, Sweden, using a MALDI-TOF instrument. Peptide mapping of the tryptic digest of the native and recombinant HSA was also done using this instrument. The results obtained from the latter analysis serve to establish the most probable primary sequence of the rHSA with reference to the known sequences of the tryptic peptides generated from purified HSA.

Matrices and Chromatography System

The chromatographic experiments were performed at room temperature (about 23° C.) using an ÄKTA™ Explorer 100 system controlled by UNICORN™ (Version 3.1) software (Amersham Biosciences, Uppsala, Sweden). The separation matrix used for step (b) is Phenyl Sepharose™ 6 Fast Flow (high sub), a regular product of Amersham Biosciences, Uppsala, Sweden. For step (c), either commercially available DEAE Sepharose™ Fast Flow (Amersham Biosciences, Uppsala, Sweden) or a modified matrix was used: Butyl Sepharose™ 6 Fast Flow (Amersham Biosciences, Uppsala, Sweden) was produced with an increased ligand density (batch U238025:160 µmol/ml) as compared to the commercial product (20-40 µmol/ml gel). This modified matrix will herein be denoted "modified Butyl-Sepharose". Furthermore, step (a) utilised a prototype matrix of HSL-type, cation-exchanger, see FIG. 1A. This medium was packed in a XK26/20 glass column as a thick suspension in 20% ethanol to obtain a bed volume of 40 ml. A linear flow rate of 300 cm/h was used. The packed column was washed with about 2 bed volumes of de-ionised water to elute most of the ethanol and then equilibrated with the appropriate buffer solution prior to sample application. The amount of buffer required for each of the chromatographic steps using the various media is shown in Table 1 below.

Buffers

Buffer A: 25 mM sodium acetate, pH 4.5

Mix 25 mL of 1 M sodium acetate and 40 mL of 1 M acetic acid and dilute to 1 L with de-ionised water. Conductivity: about 2 mS/cm at room temperature (RT).

Buffer B: 50 mM sodium phosphate, 0.1 M NaCl, 10 mM sodium caprylate, pH 7.0

Mix 155 mL 0.2 M $Na_2HPO_4$+95 mL of 0.2 M $NaH_2PO_4$+5.8 g of NaCl+1.66 g sodium caprylate and dilute to 1 L with de-ionised water. Conductivity: about 16 mS/cm at RT.

Buffer C: 50 mM sodium phosphate, 0.1 M NaCl, pH 6.0

Mix 212 mL 0.2 M $NaH_2PO_4$+38 mL of 0.2 M $Na_2HPO_4$+5.8 g of NaCl and dilute to 1 L with de-ionised water. Conductivity: 14 mS/cm at RT.

Buffer D: 50 mM sodium phosphate, 0.2 M NaCl, pH 6.0

Mix 212 mL 0.2 M $NaH_2PO_4$+38 mL of 0.2 M $Na_2HPO_4$+11.7 g of NaCl and dilute to 1 L with de-ionised water. Conductivity: 22 mS/cm at RT.

Buffer E: Cleaning-in-place (CIP) solution

30% isopropanol dissolve in 1 M NaOH solution.

EXAMPLE

Purification of rHSA

Heat Treatment of Cell Culture Supernatant (CCS)

Before cation exchange chromatography, the CCS was heat-treated primarily to inactivate proteolytic enzymes produced during fermentation of *P. pastoris*. This was performed as follows:

The frozen sample of CCS was thawed and 10 mM Na-caprylate was dissolved. The pH was adjusted to 6.0 and it was heated for 30 minutes in a water bath (maintained at 68° C. by thermostat). The sample was cooled to room temperature and its pH adjusted to 4.5. If a conventional cation exchange medium, such as SP Sepharose BB, was to be used for step (a), it would have been required to dilute the CCS 2-8 times, depending on the original conductivity of the solution, with de-ionised water to reach a conductivity of about 5-10 mS/cm (approximately 0.1 M salt concentration).

However, the HSL-type matrix used according to the present invention is much more tolerant to increased salt concentrations, and therefore the heat-treated CCS can normally be applied to step (a) without any further dilution, as long as the conductivity thereof is less than about 30 mS/cm.

The partially purified rHSA obtained after the cation exchange according to step (a) (i.e. the fraction bound to the HSL-type matrix) was also heat-treated prior to step (b) as follows: The pH of the sample was adjusted to 6.0 with 1 M NaOH and cysteine was dissolved therein to a concentration of 5 mM to serve as a reducing agent. This solution was then heated for 60 minutes in a water bath maintained at 60° C. The main purpose of this operation is to facilitate the removal of coloured substances by the HIC matrix.

Step (a): Capture Using Cation Exchange Chromatography

The cation-exchange medium was packed in an XK 16/20 column (packed bed volume 20 mL) and washed with 2 column volumes (CV) of Buffer A for equilibration. The heat-treated CCS was applied to the column via a 150 mL Superloop™ (Amersham Biosciences, Uppsala, Sweden) at a flow rate of 300 mL/h (150 cm/h). The amount of rHSA applied was about 1 g (i.e. 50 mg rHSA/ml of packed gel). After sample application, the unbound material was eluted with 3 CV of Buffer A followed by elution of the bound rHSA with 5 CV of Buffer B. The two fractions were pooled separately and the pH of the bound fraction was adjusted to 6.0 with a 1 M NaOH solution. The solution was then heated as described above, cooled to room temperature and further purified on a HIC column as described below. An 1 mL aliquot from each pooled fraction was saved for analytical purposes (i.e. to determine protein content, the $A_{350}/A_{280}$ ratio and electrophoretic analysis).

Regeneration: The column was washed with 2 CV of Buffer E to elute very strongly bound substances and restore the function of the gel. The column was allowed to stand overnight in the same solution and then washed with 4 CV of de-ionised water to elute most of the NaOH and iso-propanol. The regenerated column was re-equilibrated with 4 CV of Buffer A prior to the next cycle of adsorption/desorption process.

Step (b): Purification Step Using HIC

The rHSA-containing fraction from the previous step was transferred to a 150 mL Superloop™ and applied to an XK26/20 column packed with Phenyl Sepharose™ Fast Flow (high sub), packed bed volume 40 mL. The column was pre-equilibrated with 3 CV of Buffer C. After sample application, the column was washed with 2 CV of Buffer C to elute the unbound material that contains the rHSA. The bound material (containing mainly the 45 kDa degraded form of rHSA) was eluted with 2 CV of de-ionised water.

Regeneration: The same procedure as above.

Step (c): Polishing Step Using Weak Anion Exchange

The two fractions obtained from the previous HIC step were pooled and 1 mL aliquots from each were saved for analytical determinations (see above). A column (XK26/20) was packed with DEAE Sepharose™ Fast Flow or the above described modified Butyl-Sepharose to obtain a packed bed volume of 40 mL. Each of the packed media was washed with 2 CV of de-ionised water and then with about 5 CV of Buffer C to equilibrate them. The unbound fraction obtained from the HIC step was transferred to a 150 mL Superloop and applied to one or the other of the above two columns. The unbound fraction was eluted with 6 CV of Buffer C (from the DEAE Sepharose Fast Flow column) or with 2 CV from the modified Butyl-Sepharose column. The bound fraction was eluted with 2 CV of a 2 M solution of NaCl (for the DEAE column) or with 5 CV of Buffer D for the modified Butyl-Sepharose column. The flow rate was maintained at 90 cm/h throughout.

Regeneration: The same procedure as above.

The elution protocols optimised according to the invention for each of the media used are summarised in Table 1. The skilled person in this field can easily scale up the above-described process to pilot or production-scale operations.

TABLE 1

The number of column volumes (CV) of equilibration, elution and regeneration solutions required for each chromatography step

| Matrix | Equilibrate | Wash (Buffer) | Elute | Regenerate | Wash (De-ionised water) |
|---|---|---|---|---|---|
| HSL-type cation exchanger | 4 [A] | 3 [A] | 5 [B] | 2 [E] | 4 |
| Phe-Seph | 3 [C] | 2 [C] | 2 [*] | 2 [E] | 4 |
| DEAE-Seph | 5 [C] | 6 [C] | 2 [**] | 2 [E] | 4 |
| Modified butyl-Seph | 6 [C] | 2 [C] | 5 [D] | | 4 |

*De-ionised water
**2M NaCl

Results

Since the three step purification process is based on stepwise elution, it is easily adaptable to large-scale operation. Use of a high ligand-ButylSepharose for step (c) results in efficient removal of LMW impurities that elute as a group in the unbound fraction. Use of the high ligand-ButylSepharose also results in a better $A_{350}/A_{280}$ ratio than use of the DEAE-type of matrix for step (c).

What is claimed is:

1. A method of purifying recombinant human serum albumin (rHSA) from a cell culture supernatant (CCS), which method comprises:
    (a) subjecting said CCS to cation exchange on a bimodal high salt tolerant matrix;
    (b) followed by hydrophobic interaction chromatography (HIC);
    (c) then anion exchange; and
    (d) recovering the purified rHSA.

2. The method of claim 1, wherein the conductivity of the CCS is above about 10 when applied to step (a).

3. The method of claim 1, wherein the bimodal cation exchange matrix is capable of interacting with rHSA by charge interaction and by hydrogen bonding and/or hydrophobic interaction.

4. The method of claim 1, further comprising heat treatment of the CCS before step (a).

5. The method of claim 1, further comprising heat treatment of the product from step (a) before step (b) in the presence of a reducing agent.

6. The method of claim 1, wherein step (b) utilizes a HIC matrix including phenyl, aliphatic and/or heterocyclic ligands.

7. The method of claim 1, wherein the amount of cation exchange matrix used in step (a) is about half the amount of HIC matrix used in step (b).

8. The method of claim 1, wherein step (c) utilizes a weak anion exchanger.

9. The method of claim 8, wherein the ligand density of the weak anion exchanger is >50 μmol/ml gel/matrix.

10. The method of claim 9, wherein the purified rHSA is recovered only from the bound fraction from step (c).

11. The method of claim 8, wherein the ligand density of the weak anion exchanger is >100 μmol/ml gel/matrix.

12. The method of claim 8, wherein the ligand density of the weak anion exchanger is about 160 μmol/ml gel/matrix.

* * * * *